(12) United States Patent
Ebina

(10) Patent No.: US 9,840,257 B2
(45) Date of Patent: Dec. 12, 2017

(54) VEHICLE INFORMATION PRESENTING APPARATUS

(71) Applicant: Nissan Motor Co., Ltd., Yokohama-Shi, Kanagawa (JP)

(72) Inventor: Akihiko Ebina, Kanagawa (JP)

(73) Assignee: Nissan Motor Co., Ltd., Yokohama-shi, Kanagawa (JP)

( * ) Notice: Subject to any disclaimer, the term of this patent is extended or adjusted under 35 U.S.C. 154(b) by 0 days.

(21) Appl. No.: 15/301,296

(22) PCT Filed: Apr. 2, 2014

(86) PCT No.: PCT/JP2014/059732
§ 371 (c)(1),
(2) Date: Sep. 30, 2016

(87) PCT Pub. No.: WO2015/151243
PCT Pub. Date: Oct. 8, 2015

(65) Prior Publication Data
US 2017/0021837 A1   Jan. 26, 2017

(51) Int. Cl.
B60W 40/08      (2012.01)
G08G 1/16       (2006.01)
(Continued)

(52) U.S. Cl.
CPC .............. *B60W 40/08* (2013.01); *A61B 3/112* (2013.01); *A61B 5/0077* (2013.01); *A61B 5/024* (2013.01); *A61B 5/1103* (2013.01); *A61B 5/1123* (2013.01); *A61B 5/1128* (2013.01); *A61B 5/18* (2013.01); *A61B 5/6893* (2013.01); *B60K 28/06* (2013.01); *B60K 35/00* (2013.01);
(Continued)

(58) Field of Classification Search
CPC ........ B60W 40/08; B60W 2040/0818; B60W 2050/146; B60W 2540/02; B60W 50/14; B60K 2350/352; B60K 2350/965; B60K 28/06; B60K 35/00; G05D 1/0061; G05D 1/0088; G06K 9/00228; G06K 9/00845; G08G 1/16; A61B 5/6893
USPC ........................................................ 340/576
See application file for complete search history.

(56) References Cited
U.S. PATENT DOCUMENTS

2004/0252027 A1   12/2004   Torkkola et al.
2006/0235615 A1   10/2006   Kato et al.
(Continued)

FOREIGN PATENT DOCUMENTS

EP   2314489 A1    4/2011
JP   08-268287 A   10/1996
(Continued)

*Primary Examiner* — Hirdepal Singh
(74) *Attorney, Agent, or Firm* — Young Basile Hanlon & MacFarlane, P.C.

(57) ABSTRACT

A vehicle information presenting apparatus for use in an autonomous vehicle switches driving control between autonomous driving control, in which the vehicle is driven autonomously, and manual driving control, in which the vehicle is driven manually by a driver. The vehicle information presenting apparatus includes a driving attention level estimator configured to estimate a driving attention level of the driver, and an information presentation controller configured to switch information to present to the driver according to the driving attention level of the driver estimated by the driving attention level estimator.

15 Claims, 9 Drawing Sheets

(51) Int. Cl.

| | |
|---|---|
| *B60K 28/06* | (2006.01) |
| *B60K 35/00* | (2006.01) |
| *A61B 3/11* | (2006.01) |
| *A61B 5/00* | (2006.01) |
| *A61B 5/024* | (2006.01) |
| *A61B 5/11* | (2006.01) |
| *A61B 5/18* | (2006.01) |
| *G06K 9/00* | (2006.01) |
| *B60W 50/08* | (2012.01) |
| *B60W 50/14* | (2012.01) |
| *G05D 1/00* | (2006.01) |

(52) U.S. Cl.
CPC .......... *B60W 50/082* (2013.01); *B60W 50/14* (2013.01); *G06K 9/00228* (2013.01); *G06K 9/00845* (2013.01); *G08G 1/16* (2013.01); *B60K 2350/352* (2013.01); *B60K 2350/962* (2013.01); *B60K 2350/965* (2013.01); *B60W 2040/0818* (2013.01); *B60W 2040/0872* (2013.01); *B60W 2050/146* (2013.01); *B60W 2540/02* (2013.01); *G05D 1/0061* (2013.01); *G05D 1/0088* (2013.01)

(56) References Cited

U.S. PATENT DOCUMENTS

| | | | | |
|---|---|---|---|---|
| 2006/0255956 | A1* | 11/2006 | Arakawa | B60K 28/066 340/576 |
| 2008/0243390 | A1* | 10/2008 | Nakamori | G06K 9/00805 701/301 |
| 2010/0030434 | A1* | 2/2010 | Okabe | A61B 5/165 701/48 |
| 2015/0284009 | A1* | 10/2015 | Cullinane | B60W 30/00 701/23 |
| 2016/0082978 | A1* | 3/2016 | Ozaki | G01C 21/34 701/58 |
| 2016/0214483 | A1* | 7/2016 | Kleen | B60W 50/14 |
| 2016/0280234 | A1* | 9/2016 | Reilhac | B60K 35/00 |
| 2016/0297449 | A1* | 10/2016 | Heim | B60W 40/09 |
| 2017/0028987 | A1* | 2/2017 | Yamada | B60W 50/08 |

FOREIGN PATENT DOCUMENTS

| | | |
|---|---|---|
| JP | 09-160643 A | 6/1997 |
| JP | 10-288532 A | 10/1998 |
| JP | 2006-318446 A | 11/2006 |
| JP | 2008-191778 A | 8/2008 |
| WO | 2013-132961 A1 | 9/2013 |

\* cited by examiner

VEHICLE INFORMATION PRESENTING APPARATUS

TECHNICAL FIELD

The present invention relates to a vehicle information presenting apparatus which is applied to a vehicle with an autonomous driving capability and is configured to present information regarding the travelling condition of the vehicle.

BACKGROUND

An information presenting apparatus capable of informing a driver of information regardless of change in the posture, the age, or the like of the driver is conventionally known (Japanese Patent Application Publication No. 2008-191778). Japanese Patent Application Publication No. 2008-191778 informs a driver of information by changing the width of an attention calling frame or adjusting the amount of light stimulation according to the driver's angle of vision.

Japanese Patent Application Publication No. 2008-191778 constantly gives information to the driver. During autonomous driving, a driver is likely to pay a low level of attention to driving. Excessive information presentation to such a driver might burden the driver with an increased monitoring task.

SUMMARY

The present invention has been made in view of the above problem, and aims to provide a vehicle information presenting apparatus capable of presenting appropriate information to an occupant according to the condition of the occupant during autonomous driving.

A vehicle information presenting apparatus according to an aspect of the present invention estimates a driving attention level of a driver and switches information to present to the driver according to the estimated driving attention level of the driver.

DETAILED DESCRIPTION OF THE EMBODIMENTS

Embodiments of the present invention are described below with reference to the drawings.

First Embodiment

Figure 1:
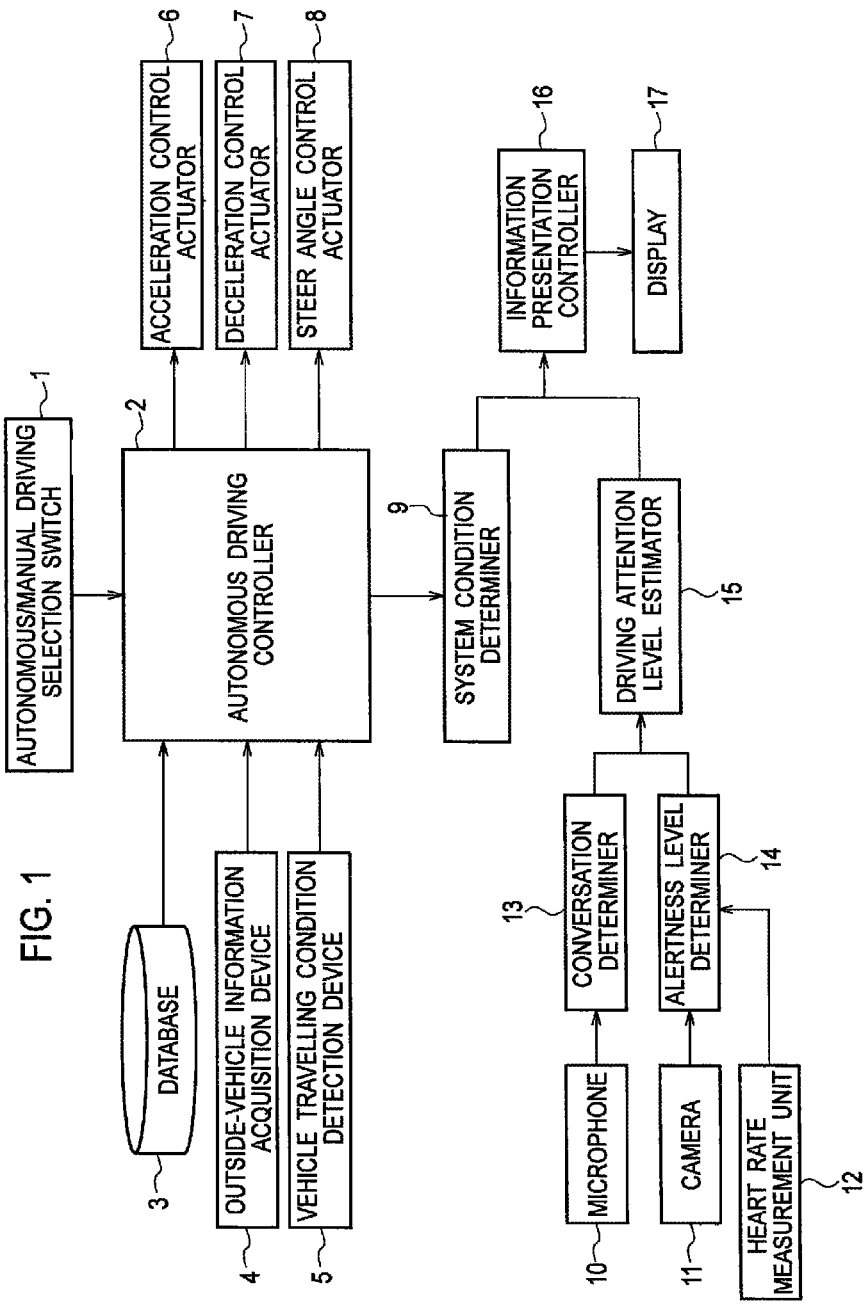
FIG. 1 is a block diagram showing the configuration of an autonomous vehicle to which a vehicle information presenting apparatus according to a first embodiment of the present invention is applied.

As shown in FIG. 1, an autonomous vehicle (simply called a vehicle hereinbelow) mainly includes an autonomous/manual driving selection switch 1, an autonomous driving controller 2, a system condition determiner 9, a driving attention level estimator 15, an information presentation controller 16, and a display 17.

The autonomous/manual driving selection switch 1 is operated by a driver to select and switch between autonomous driving and manual driving of the vehicle. For example, the autonomous/manual driving selection switch 1 is placed near the driver's seat of the vehicle.

The autonomous driving controller 2 is a computer integrally including a CPU and a recording unit such as a RAM, a ROM, and a hard disk. The autonomous driving controller 2 is configured to perform autonomous driving control of the vehicle based on the travelling condition of the vehicle and information on the outside of the vehicle (outside-vehicle information), when autonomous driving has been selected by the driver with the autonomous/manual driving selection switch 1. More specifically, the autonomous driving controller 2 acquires the outside-vehicle information by using database 3, such as maps and traffic information, and an outside-vehicle information acquisition device 4 (e.g., a camera or a laser sensor). The autonomous driving controller 2 detects the travelling condition of the vehicle by using a vehicle travelling condition detection device 5 (e.g., a vehicle speed sensor). Then, the autonomous driving controller 2 determines a travel route to a destination based on the information in the database 3, and controls various control actuators 6, 7, and 8 based on the outside-vehicle information and the travelling condition of the vehicle so that the vehicle may travel according to the travel route. The vehicle is thus autonomously driven by the autonomous driving controller 2.

The system condition determiner 9 determines an autonomous driving system condition by using information outputted from the autonomous driving controller 2. The autonomous driving system condition indicates operation statuses of the outside-vehicle information acquisition device 4, such as a camera, and the various control actuators 6, 7, and 8. When these devices are in working order, the system condition determiner 9 determines that the system condition is normal. When being unable to acquire the outside-vehicle information due to camera failure or the like, the system condition determiner 9 determines that the system condition is abnormal.

When the autonomous driving system condition is normal, the system condition determiner 9 can classify the system condition as favorable or unfavorable according to travelling environments. The travelling environments include the weather and road conditions. The system condition is classified as favorable when the devices are delivering sufficient performance. The system condition is classified as unfavorable when any of the devices is not delivering sufficient performance. To be more specific, the cases where the system condition determiner 9 determines that the system condition is unfavorable because any of the devices is not delivering sufficient performance include a case where the camera can recognize only the vicinity thereof due to bad weather (such as heavy rain, snow, or fog), a case where the laser sensor provides only low sensing accuracy due to darkness or backlight, a case where the camera cannot recognize the lanes due to poor road conditions (because, e.g., the white line has been worn away or the road is a dirt road), and a case where the camera cannot decide a travelling path due to road work.

A conversation determiner 13 is a device that recognizes voice generated within the vehicle compartment. The conversation determiner 13 recognizes and analyzes the voice of the driver picked up by a microphone 10. The conversation determiner 13 recognizes the voice of the driver using voice data on the driver prerecorded to distinguish the voice of the driver from the voice of others. The conversation includes one between the driver and another occupant and one between the driver and the vehicle. A speaker (not shown) is installed in the vehicle compartment. Through this speaker, the vehicle information presenting apparatus can start various types of conversations (which may be a daily conversation or a quiz) for the driver. Then, the conversation determiner 13 recognizes and analyzes speech (voice) of the driver in this conversation. Even when multiple occupants are in the vehicle, the vehicle information presenting apparatus may start a conversation for the driver through the speaker.

A camera 11 is a device that captures the facial images of the driver. The camera 11 includes an image pickup element such as a CCD or a CMOS, and is placed near the room mirror or on the dashboard. The shooting angle of the camera 11 can be changed appropriately. The camera 11 can capture not only the facial images but also an action of the driver on the seat (e.g., an action of the driver adjusting themselves on the seat). Note that the camera 11 is different from the camera in the outside-vehicle information acquisition device 4.

A heart rate measurement unit 12 is located in a part of the steering wheel and measures the heart rate of the driver when the driver holds this part with both hands. Alternatively, the heart rate measurement unit 12 may be a contactless sensor incorporated in the seat.

An alertness level determiner 14 is a device that determines the alertness level of the driver. The alertness level determiner 14 determines the alertness level of the driver by monitoring the eye movement of the driver, such as the pupil diameter or the number of blinks, using the facial images of the driver captured by the camera 11, the facial images being subjected to various kinds of image processing, such as gray scaling, edge detection, and pattern matching. The alertness level determiner 14 determines the alertness level of the driver also by monitoring the heart rate of the driver measured by the heart rate measurement unit 12.

The driving attention level estimator 15 is a device that estimates the attention level of the driver about driving. The driving attention level estimator 15 estimates the driving attention level of the driver based on the voice of the driver analyzed by the conversation determiner 13 and the alertness level of the driver determined by the alertness level determiner 14.

The information presentation controller 16 switches information to present on the display 17 according to the autonomous driving system condition and the driving attention level of the driver. Specifically, the information presentation controller 16 switches between information regarding the system condition (called system condition information hereinbelow) and information regarding driving assistance (called driving assistance information hereinbelow). The system condition information indicates whether the system condition is normal or abnormal and, when the system condition is normal, additionally indicates whether the system condition is favorable or unfavorable. A detailed description for the driving assistance information will be given later.

The display 17 presents various pieces of information to the driver, and is placed, for example, near the driver's seat of the vehicle. The display 17 may be placed at a position where information can be presented not only to the driver but also to other occupants.

The system condition determiner 9, the conversation determiner 13, the alertness level determiner 14, the driving attention level estimator 15, and the information presentation controller 16 are configured as a computer integrally including a CPU and a recording unit such as a RAM, a ROM, and a hard disk.

Figure 2A:
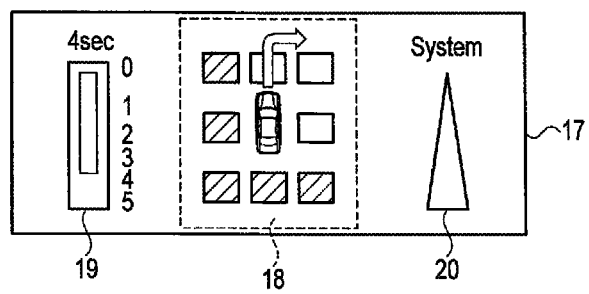
FIGS. 2(a) and 2(b) show two examples of driving assistance information presented on a display.
Figure 2B:
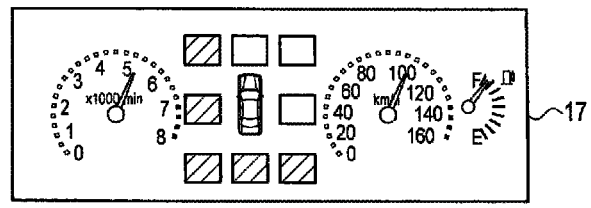

Next, with reference to FIG. 2, two examples are given of the driving assistance information presented on the display 17 by the information presentation controller 16. The driving assistance information shows obstacles on a travelling path, a travelling direction, or the like to help a smooth transition from autonomous driving to manual driving. As FIG. 2(*a*) shows, images 18 to 20 are presented on the display 17. The image 18 indicates obstacles on a travelling path and a travelling direction. Shaded rectangles indicate areas where the vehicle cannot travel, and unshaded rectangles indicate areas where the vehicle can travel. Thus, the image 18 indicates that the road on which the vehicle is travelling has two lanes. The arrow in the image 18 indicates that the vehicle is turning right at the next intersection. The image 19 indicates that the vehicle is turning right in four seconds. The image 20 is a triangular image which indicates the autonomous driving system condition and changes in color according to the system condition. Colors of the image 20 are not limited. For example, the image 20 turns green when the system condition is favorable and turns red when the system condition is unfavorable. It is desirable that colors that people can easily understand what they mean be selected, such as red (danger), yellow (caution), and green (normal), for example. The information presentation controller 16 may also change the color of the image 20 gradationally according to the value of a system confidence level S1 to be described later. As shown in FIG. 2(*b*), the information presentation controller 16 may present a tachometer, a speedometer, and a fuel gauge as the driving assistance information.

Figure 3A:
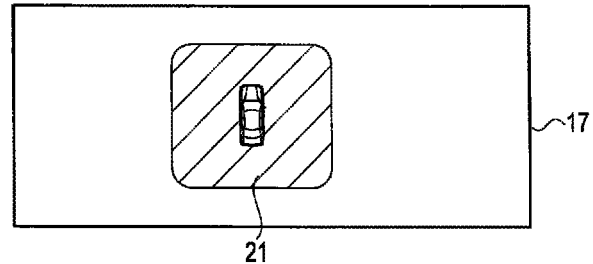
FIGS. 3(a) and 3(b) show two examples of system condition information presented on the display.
Figure 3B:
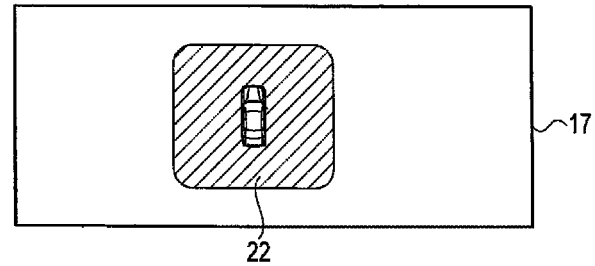

Next, with reference to FIG. 3, two examples are given of the autonomous driving system condition information presented on the display 17 by the information presentation controller 16. When the system condition is favorable, the information presentation controller 16 presents an image 21 in which a vehicle-shaped mark is superimposed on a green rectangle, as shown in FIG. 3(*a*). When the system condition is unfavorable, the information presentation controller 16 presents an image 22 in which a vehicle-shaped mark is superimposed on a red rectangle, as shown in FIG. 3(*b*). By being presented with one of such simple images that differ only in color, the driver can see at a single glance whether the system condition is favorable or unfavorable. When the system condition is unfavorable, the image 22 may be blinked, rotated, or outlined to call for attention from the driver. When the system condition is abnormal, the information presentation controller 16 displays nothing on the display 17, or presents the image 22 in a larger size than when the system condition is unfavorable. By thus making an emphatic presentation when the system condition is abnormal, the information presentation controller 16 can call driver's attention strongly.

Figure 4:
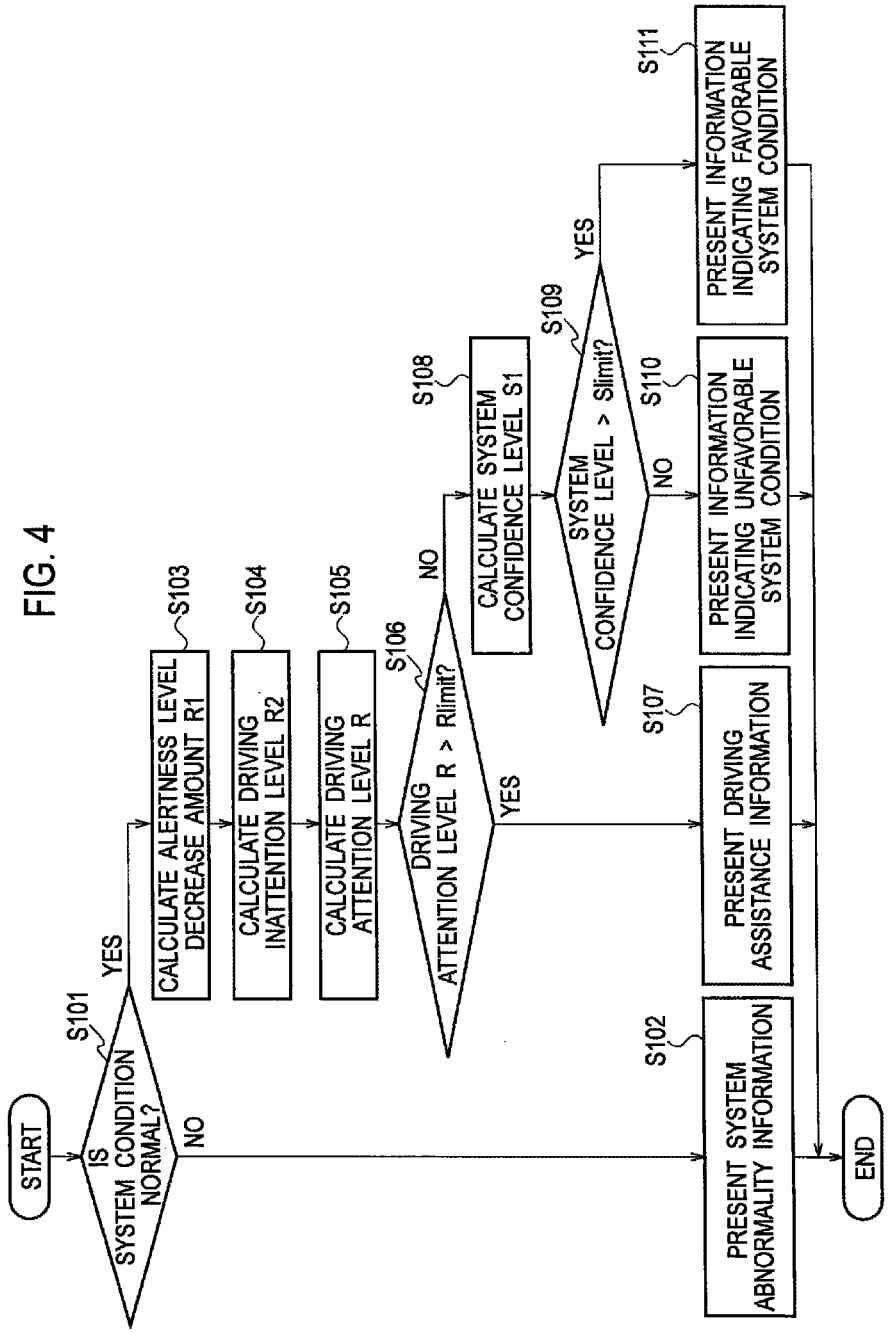
FIG. 4 is a flowchart illustrating information presentation processing performed by the vehicle information presenting apparatus according to the first embodiment.

Next, with reference to the flowchart in FIG. 4, a description is given of information presenting processing performed by the vehicle information presenting apparatus. This flowchart starts when autonomous driving is selected with the switch.

First, in Step S101, the system condition determiner 9 determines whether the autonomous driving system condition is normal. The processing proceeds to Step S103 when the system condition is normal, and proceeds to Step S102 when the system condition is not normal.

In Step S102, the information presentation controller 16 presents, on the display 17, information indicating that the autonomous driving system condition is abnormal, and thus ends the processing.

When the processing proceeds to Step S103, the alertness level determiner 14 calculates an alertness level decrease amount R1 (%). The alertness level decrease amount R1 is an index of how much the alertness level of the driver is decreased. The alertness level determiner 14 determines that the driver has a lower alertness level when the alertness level decrease amount R1 shows a higher number. The alertness level decrease amount R1 is expressed as follows using alertness level decrease coefficients R11, R12, and R13:

$$R1=R11 \times R12 \times R13 \times 100.$$

The alertness level decrease coefficients R11, R12, and R13 are described with reference to FIG. 5. As with the alertness level decrease amount R1, the alertness level decrease coefficients R11, R12, and R13 are indices of how much the alertness level of the driver is decreased.

Figure 5A:
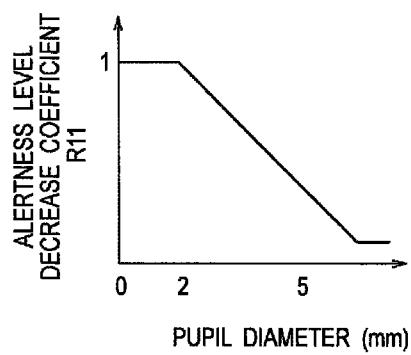
FIG. 5(a) is a graph showing the relation between an alertness level decrease coefficient R11 and the pupil diameter of a driver.
Figure 5B:
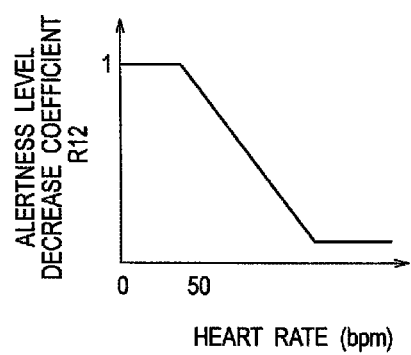
FIG. 5(b) is a graph showing the relation between an alertness level decrease coefficient R12 and the heart rate of a driver.
Figure 5C:
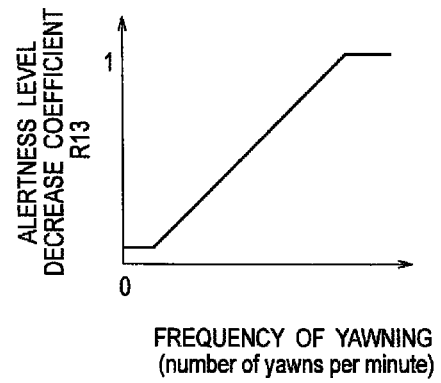
FIG. 5(c) is a graph showing the relation between an alertness level decrease coefficient R13 and the frequency of yawning.

FIG. 5(*a*) is a graph showing the relation between the alertness level decrease coefficient R11 and the pupil diameter of a driver. The alertness level decrease coefficient R11 is 1 when the pupil diameter is up to 2 mm, and decreases as the pupil diameter increases from 2 mm.

FIG. 5(*b*) is a graph showing the relation between the alertness level decrease coefficient R12 and the heart rate of a driver. The alertness level decrease coefficient R12 is 1 when the heart rate is up to 50 bpm, and decreases as the heart rate increases from 50 bpm.

FIG. 5(*c*) is a graph showing the relation between the alertness level decrease coefficient R13 and the frequency of yawning of a driver. The alertness level decrease coefficient R13 approaches 1 as the number of yawns per a predetermined period of time increases.

The alertness level determiner 14 thus calculates the alertness level decrease amount R1 using the alertness level decrease coefficients R11 to R13. Although the alertness level decrease amount R1 is calculated using the alertness level decrease coefficients R11 to R13 in the present embodiment, the alertness level decrease amount R1 may be calculated using only one or two of the alertness level decrease coefficients R11 to R13. Indices of the alertness level of a driver are not limited to the ones given above. For example, the length of a blink of a driver, the frequency of eye-rubbing of a driver, or a period of time in which the eyeballs are motionless may be used to calculate the alertness level decrease amount R1.

Next, in Step S104, the conversation determiner 13 calculates a driving inattention level R2 (%). The driving inattention level R2 is an index of how much the driver is not paying attention to driving. The conversation determiner 13 determines that the driver is paying less attention to driving when the driving inattention level R2 shows a higher number. The driving inattention level R2 is expressed as follows using driving inattention coefficients R21, R22, and R23:

$$R2=R21 \times R22 \times R23 \times 100.$$

The driving inattention coefficients R21 to R23 are described with reference to FIG. 6. As with the driving inattention level R2, the driving inattention coefficients R21 to R23 are indices of how much the driver is not paying attention to driving.

Figure 6A:
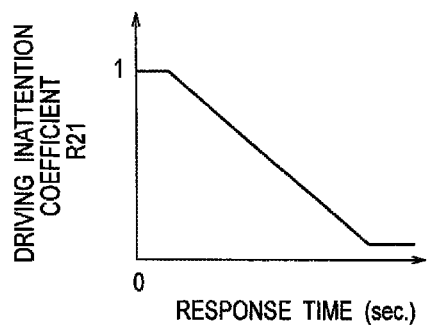
FIG. 6(a) is a graph showing the relation between a driving inattention coefficient R21 and a response time.
Figure 6B:
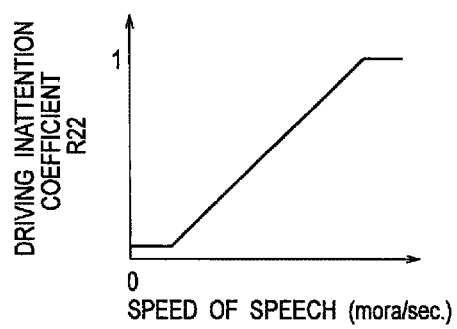
FIG. 6(b) is a graph showing the relation between a driving inattention coefficient R22 and the speed of speech.
Figure 6C:
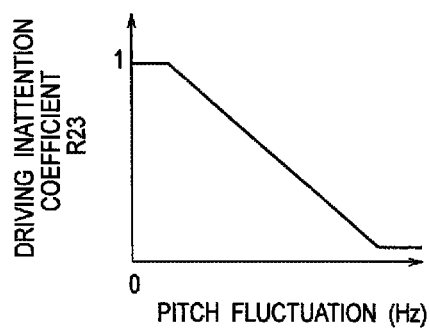
FIG. 6(c) is a graph showing the relation between a driving inattention coefficient R23 and [[a]] pitch fluctuation.

FIG. 6(*a*) is a graph showing the relation between the driving inattention coefficient R21 and a response time. The response time is the length of time that elapses before the driver responds to a conversation with another occupant or the vehicle. The shorter the response time, the more the driving inattention coefficient R21 approaches 1, because a shorter response time indicates that the driver is more concentrated on the conversation.

FIG. 6(*b*) is a graph showing the relation between the driving inattention coefficient R22 and the speed of speech. The speed of speech is the speed in which a driver speaks. The higher the speed of speech, the more the driving inattention coefficient R22 approaches 1, because a higher speed of speech indicates that the driver is more concentrated on the conversation.

FIG. 6(*c*) is a graph showing the relation between the driving inattention coefficient R23 and pitch fluctuation. The pitch fluctuation is the frequency of the voice of a driver. The smaller the pitch fluctuation, the more the driving inattention coefficient R23 approaches 1, because smaller pitch fluctuation indicates that the driver is more concentrated on the conversation.

As described, the conversation determiner 13 calculates the driving inattention level R2 using the driving inattention coefficient R21 to R23. Although the driving inattention level R2 is calculated using the driving inattention coefficients R21 to R23 in the present embodiment, the driving inattention level R2 may be calculated using only one or two of the driving inattention coefficients R21 to R23.

Next, in Step S105, the driving attention level estimator 15 calculates a driving attention level R (%). The driving attention level R is an index of how much the driver is paying attention to driving. The driving attention level estimator 15 determines that the driver is paying more attention to driving when the driving attention level R shows a higher number. The driving attention level R is expressed as follows using the alertness level decrease amount R1 and the driving inattention level R2:

$$R=(100-R1)\times(100-R2)/100.$$

The driving attention level R may also be calculated using only one of the alertness level decrease amount R1 and the driving inattention level R2. In this case, zero is inserted for the value of the unused index.

Next, in Step S106, the information presentation controller 16 determines whether the driving attention level R is higher than Rlimit (a predetermined value). The processing proceeds to Step S107 when the driving attention level R is higher than Rlimit, and proceeds to Step S108 when the driving attention level R is equal to or lower than Rlimit.

In Step S107, the information presentation controller 16 presents the driving assistance information on the display 17, and ends the processing.

In Step S108, on the other hand, the system condition determiner 9 calculates a system confidence level S1 (%). The system confidence level S1 is an index of how favorable the autonomous driving system condition is. The system condition determiner 9 determines that the system condition is more favorable when the system confidence level S1 shows a higher value. The system confidence level S1 is expressed as follows using system confidence coefficients S11, S12, and S13:

$$S1=S11\times S12\times S13\times 100.$$

The system confidence coefficients S11 to S13 are described with reference to FIG. 7. As with the system confidence level S1, the system confidence coefficients S11 to S13 are indices of how favorable or unfavorable the system condition is.

Figure 7A:
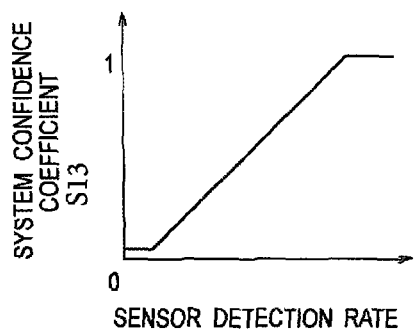
FIG. 7(a) is a graph showing the relation between a system confidence coefficient S11 and a sensor detection rate.

FIG. 7(a) is a graph showing the relation between the system confidence coefficient S11 and a sensor detection rate. The sensor detection rate is a value obtained by dividing the capability of, e.g., a laser sensor under current travelling conditions by the maximum capability of the laser sensor. More specifically, in a case of a laser sensor capable of detecting an obstacle up to 200 meters ahead, the laser sensor has a sensor detection rate of 0.5 if the laser sensor can detect only an obstacle 100 meters ahead due to a poor environment such as rain or fog. The higher the sensor detection rate, the more the system confidence coefficient S11 approaches 1, because a higher sensor detection rate indicates that the system condition is more favorable.

Figure 7B:
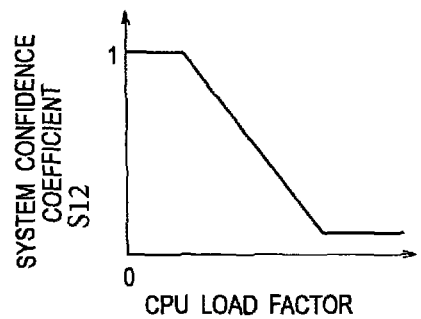
FIG. 7(b) is a graph showing the relation between a system confidence coefficient S12 and a CPU load factor.

FIG. 7(b) is a graph indicating the relation between the system confidence coefficient S12 and a CPU load factor. The CPU load factor is the load factor of the CPU for the autonomous driving control under current travelling conditions. The lower the CPU load factor, the more the system confidence coefficient S12 approaches 1, because a lower CPU load factor indicates that the system condition is more favorable.

Figure 7C:
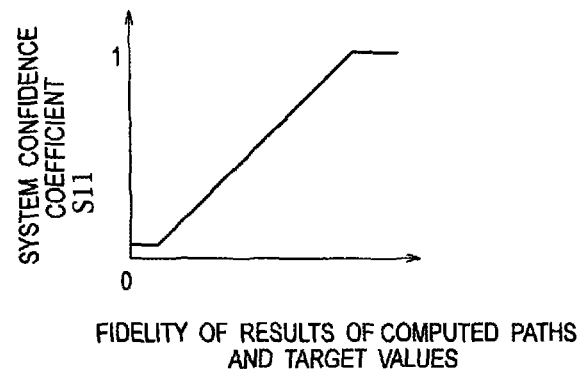
FIG. 7(c) is a graph showing the relation between a system confidence coefficient S13 and the fidelity of results of computed paths and target values.

FIG. 7(c) is a graph showing the relation between the system confidence coefficient S13 and the fidelity of results of computed paths and target values. The fidelity of results of computed paths and target values is an index numerically indicating whether the autonomously-driven vehicle is travelling on a set travelling route. A higher number of the fidelity indicates that the autonomously-driven vehicle is travelling on a set travelling route, and a lower number of the fidelity indicates that the autonomously-driven vehicle is travelling on a route different from the set travelling route. For example, the fidelity of results of computed paths and target values shows a low value when the autonomous driving system cannot recognize the set travelling route due to worn-away lane lines or road work and drives the vehicle on a different route. Thus, a lower value of the fidelity indicates that the autonomous driving system condition is more unfavorable. In other words, the higher the value of the fidelity, the more the system confidence coefficient S13 approaches 1, because a higher value indicates that the system condition is more favorable.

As described, the system condition determiner 9 calculates the system confidence level S1 using the system confidence coefficients S11 to S13. Although the system confidence level S1 is calculated using the system confidence coefficients S11 to S13 in the present embodiment, the system confidence level S1 may be calculated using only one or two of the system confidence coefficients S11 to S13.

Next, in Step S109, the information presentation controller 16 determines whether the system confidence level S1 is higher than Slimit (a predetermined value). The processing proceeds to Step S111 when the system confidence level S1 is higher than Slimit, and proceeds to Step S110 when the system confidence level S1 is equal to or lower than Slimit.

In Step S110, the information presentation controller 16 presents, on the display 17, information indicating that the autonomous driving system condition is unfavorable, and ends the processing.

In Step S111, on the other hand, the information presentation controller 16 presents, on the display 17, information indicating that the autonomous driving system condition is favorable, and ends the processing.

As described above, the vehicle information presenting apparatus of the present application estimates the driving attention level R of a driver, and switches information to present on the display 17 according to the estimated driving attention level R of the driver. The vehicle information presenting apparatus can provide the driver with appropriate information by switching information to present on the display 17 between information that gives the driver reassurance about autonomous driving and information that calls attention from the driver.

The vehicle information presenting apparatus of the present embodiment determines the autonomous driving system condition, and presents the system condition on the display 17 when the driving attention level R of the driver is equal to or lower than Rlimit. A driver might be bothered if the driving assistance information is presented to the driver when the driver is paying a low level of attention to driving. For this reason, when the driver is paying a low level of attention to driving, the vehicle information presenting apparatus of the present embodiment avoids bothering the driver by presenting the system condition to the driver using a simple image. In addition, the driver can monitor the autonomous driving with less effort because the driver can see the system condition at a single glance.

The vehicle information presenting apparatus of the present embodiment calculates the system confidence level S1 indicating whether the autonomous driving system condition is favorable or unfavorable, and presents, on the display 17, information indicating that the system condition is unfavorable when the system confidence level S1 is equal to or lower than Slimit. As this information, the vehicle information presenting apparatus presents the red image 22 which is easy to catch the eye of the driver, and can thereby call attention from the driver who is paying a low level of attention to driving. This elevates the driving attention level of the driver, preventing a situation where the driver is flustered when the driving mode suddenly switches from autonomous driving to manual driving.

When the system confidence level S1 is higher than Slimit, the vehicle information presenting apparatus of the present embodiment presents, on the display 17, information indicating that the system condition is favorable. As this information, the vehicle information presenting apparatus presents the green image 21. The driver can thereby see at a single glance that the system condition is favorable, feeling reassured about autonomous driving.

The vehicle information presenting apparatus of the present embodiment detects the condition of the driver and thereby estimates the driving attention level R. The vehicle information presenting apparatus can thus accurately estimate the driving attention level R of the driver.

The vehicle information presenting apparatus of the present embodiment detects the voice of the driver from a conversation held in the vehicle compartment, and estimates the driving attention level R of the driver based on that detected voice. The vehicle information presenting apparatus can thus accurately estimate the driving attention level R of the driver.

The vehicle information presenting apparatus of the present embodiment detects at least one of a response time, the speed of speech, and pitch fluctuation of the driver in a conversation held in the vehicle compartment. The vehicle information presenting apparatus can thus accurately estimate the driving attention level R of the driver.

In addition, the vehicle information presenting apparatus of the present embodiment estimates the driving attention level R of the driver using the facial image and the heart rate of the driver. The vehicle information presenting apparatus can thus accurately estimate the driving attention level R of the driver.

From the facial images of the driver, the vehicle information presenting apparatus of the present embodiment detects at least one of the pupil diameter, the frequency of yawning, the length of a blink, and the frequency of eye-rubbing. The vehicle information presenting apparatus can thus accurately estimate the driving attention level R of the driver.

The vehicle information presenting apparatus of the present embodiment presents, on the display 17, the driving assistance information when the driving attention level R is higher than Rlimit. By checking the driving assistance information, which contains information such as obstacles on a travelling path and a travelling direction, the driver can smoothly transition from autonomous driving to manual driving. In other words, the driver can take over driving without haste, feeling reassured about autonomous driving.

When determining that the system condition is abnormal, the vehicle information presenting apparatus of the present embodiment presents information indicative of system condition abnormality on the display 17 emphatically. Thus, the vehicle information presenting apparatus can call driver's attention strongly.

In the present embodiment, the system condition information contains less information than the driving assistance information, as shown in FIGS. 2 and 3. The vehicle information presenting apparatus in the present embodiment presents such system condition information when the driver is paying a low level of attention to driving. Thus, the vehicle information presenting apparatus presents less amount of information to a driver who is paying a low level of attention to driving. By reducing the amount of information to present, the vehicle information presenting apparatus can provide appropriate information to the driver paying a low level of attention to driving.

Second Embodiment

Next, a second embodiment of the present invention is described. The second embodiment differs from the first embodiment in that a posture is used instead of a voice to estimate the driving attention level. The same parts as those in the first embodiment are denoted by the same reference numerals as those used in the first embodiment, and are not described in detail again.

Figure 8:
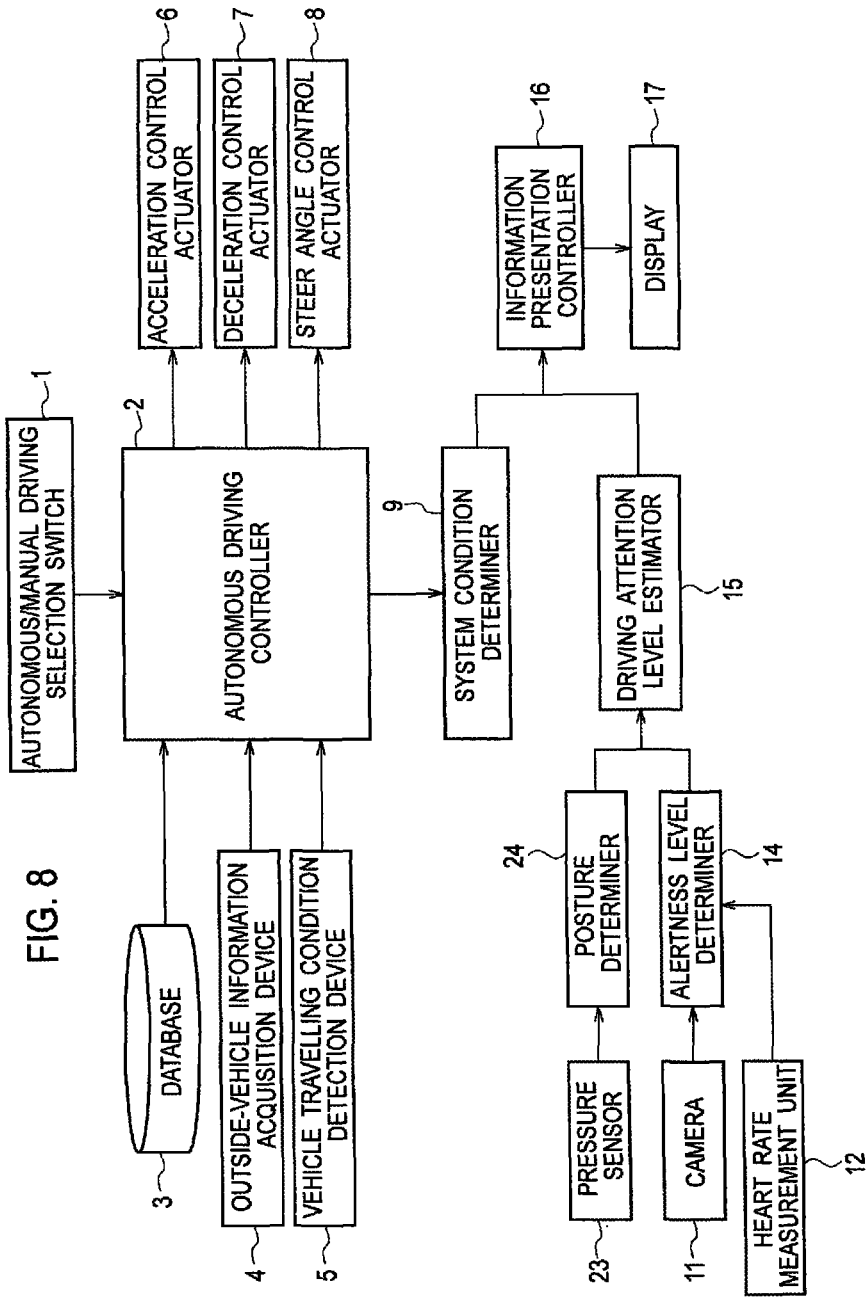
FIG. 8 is a block diagram showing the configuration of an autonomous vehicle to which a vehicle information presenting apparatus according to a second embodiment of the present invention is applied.

As shown in FIG. 8, a vehicle information presenting apparatus of the second embodiment is different from the vehicle information presenting apparatus of the first embodiment in including a pressure sensor 23 and a posture determiner 24 in place of the microphone 10 and the conversation determiner 13.

The pressure sensor 23 is a pressure-sensitive sensor that detects the posture of an occupant, and is embedded in the backrest of the seat.

The posture determiner 24 is a device that determines the posture of the occupant based on a pressure applied to the seat backrest, which is detected by the pressure sensor 23. The posture determiner 24 is configured as a computer integrally including a CPU and a recording medium such as a RAM, a ROM, and a hard disk. In the present embodiment, the pressure sensor 23, the camera 11, and the heart rate measurement unit 12 are placed in the vehicle compartment to be able to acquire not only data on the driver, but also data on other occupants.

Figure 9:
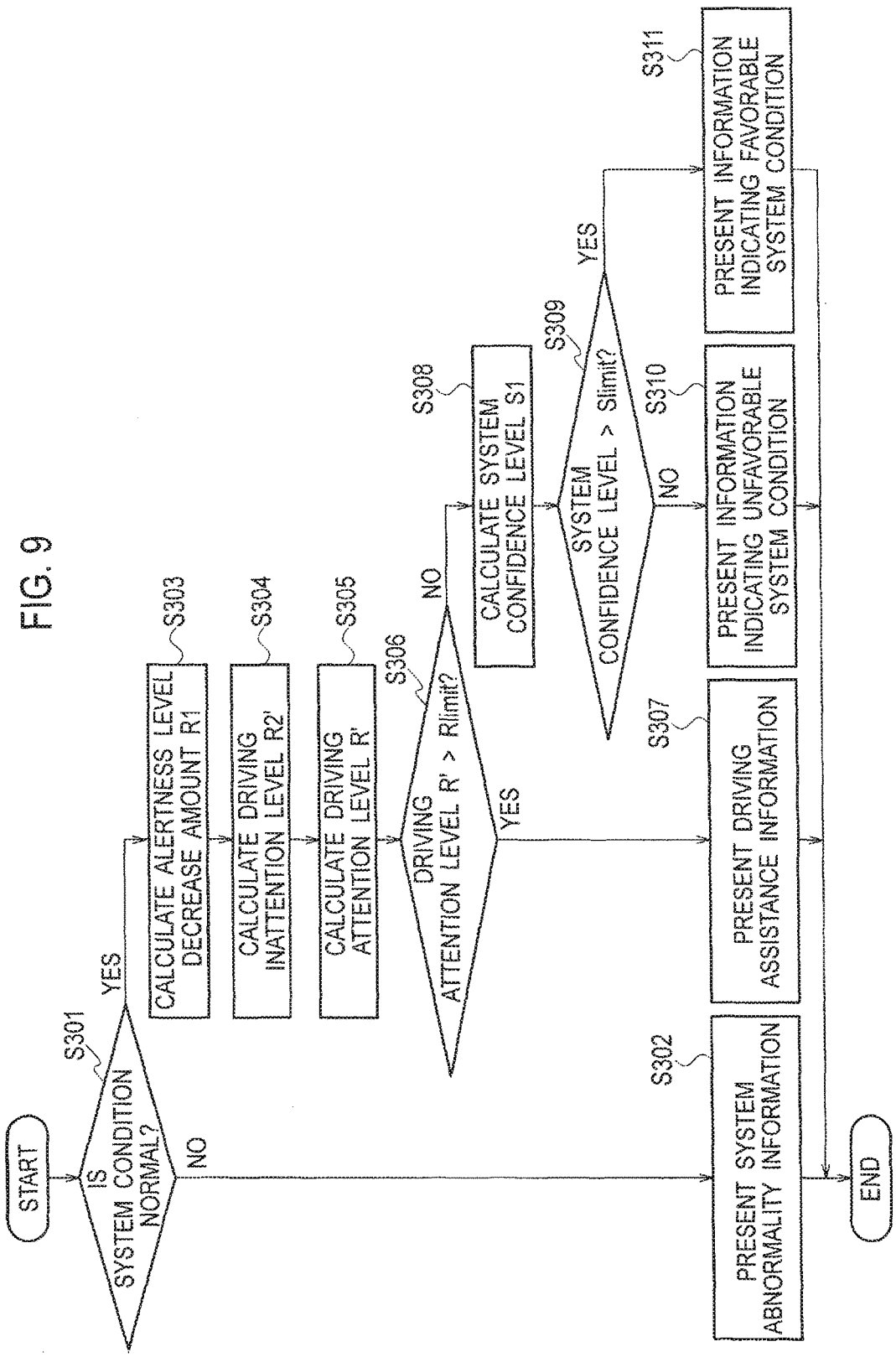
FIG. 9 is a flowchart illustrating information presentation processing performed by the vehicle information presenting apparatus according to the second embodiment.

Next, with reference to the flowchart in FIG. 9, a description is given of information presenting processing performed by the vehicle information presenting apparatus. This flowchart starts when autonomous driving is selected with the switch.

First, in Step S301, the system condition determiner 9 determines whether the autonomous driving system condition is normal. The processing proceeds to Step S303 when the system condition is normal, and proceeds to Step S302 when the system condition is not normal.

In Step S302, the information presentation controller 16 presents, on the display 17, information indicating that the autonomous driving system condition is abnormal, and thus ends the processing.

When the processing proceeds to Step S303, the alertness level determiner 14 calculates the alertness level decrease amount R1.

Next, in Step S304, the posture determiner 24 calculates a driving inattention level R2' (%). The driving inattention level R2' is an index of how much an occupant is not paying attention to driving. The conversation determiner 13 determines that the occupant is paying less attention to driving when the driving inattention level R2' shows a higher number. The driving inattention level R2' is expressed as follows using a driving inattention coefficient R24:

$$R2'=R24\times 100.$$

The driving inattention coefficient R24 is described with reference to FIG. 10. As with the driving inattention level R2', the driving inattention coefficient R24 is an index of how much the occupant is not paying attention to driving.

Figure 10:
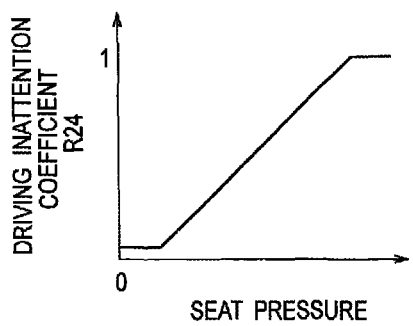
FIG. 10 is a graph showing the relation between a driving inattention coefficient R24 and a seat pressure.

FIG. 10 is a graph showing the relation between the driving inattention coefficient R24 and a seat pressure. The seat pressure is a pressure applied to the seat backrest. As an occupant reclines the backrest relative to the seat cushion by adjusting the angle of the seat backrest, the seat pressure increases, and the driving inattention coefficient R24 approaches 1. In other words, the more relaxed posture the occupant makes by reclining the seat backrest, the more the driving inattention coefficient R24 approaches 1. The driving inattention level R2' may alternatively be calculated using an output from a reclining sensor provided in the seat to sense reclining.

Next, in Step S305, the driving attention level estimator 15 calculates a driving attention level R' (%). The driving attention level R' is an index of how much an occupant is paying attention to driving. The driving attention level estimator 15 determines that the occupant is paying more attention to driving when the driving attention level R' shows a higher value. The driving attention level R' is expressed as follows using the alertness level decrease amount R1 and the driving inattention level R2':

$$R'=(100-R1)\times(100-R2')/100.$$

The driving attention level R' may also be calculated using only one of the alertness level decrease amount R1 and the driving inattention level R2'. In this case, zero is inserted for the value of the unused index.

Next, in Step S306, the information presentation controller 16 determines whether the driving attention level R' is higher than Rlimit (a predetermined value). The processing proceeds to Step S307 when the driving attention level R' is higher than Rlimit, and proceeds to Step S308 when the driving attention level R' is equal to or lower than Rlimit.

In Step S307, the information presentation controller 16 presents the driving assistance information on the display 17, and ends the processing.

In Step S308, on the other hand, the system condition determiner 9 calculates the system confidence level S1.

Next, in Step S309, the information presentation controller 16 determines whether the system confidence level S1 is higher than Slimit (a predetermined value). The processing proceeds to Step S311 when the system confidence level S1 is higher than Slimit, and proceeds to Step S310 when the system confidence level S1 is equal to or lower than Slimit.

In Step S310, the information presentation controller 16 presents, on the display 17, information indicating that the autonomous driving system condition is unfavorable, and ends the processing.

In Step S311, on the other hand, the information presentation controller 16 presents, on the display 17, information indicating that the autonomous driving system condition is favorable, and ends the processing.

As described above, the vehicle information presenting apparatus of the present embodiment detects the posture of an occupant and estimates the driving attention level R' of the occupant based on the detected posture of the occupant. Then, the vehicle information presenting apparatus switches information to present on the display 17 according to the estimated driving attention level R' of the occupant. The vehicle information presenting apparatus can provide the occupant with appropriate information by switching information to present on the display 17 between information that gives reassurance about autonomous driving and information that calls for attention from the driver. The vehicle information presenting apparatus monitors not only the driver but also an occupant other than the driver to be able to estimate the driving attention level R' of the occupants including the driver. The vehicle information presenting apparatus can thus switch the information according to the driving attention level R' of the occupants including the driver, so that an occupant other than the driver can also be given a sense of reassurance about autonomous driving.

The above embodiments are provided to present examples of the application of the present invention, and are not intended to limit the technical scope of the present invention to what is disclosed as the embodiments. Thus, the technical scope of the present invention is not limited to the specific technical matters disclosed in the above embodiments, and encompasses various modifications, changes, alternate techniques, and the like which can be easily led from the disclosure herein.

Figure 11A:
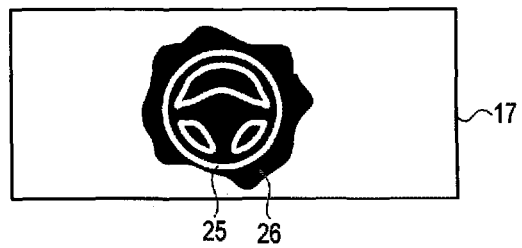
FIGS. 11(a) and 11(b) show other examples of driving assistance information presented on the display.
Figure 11B:
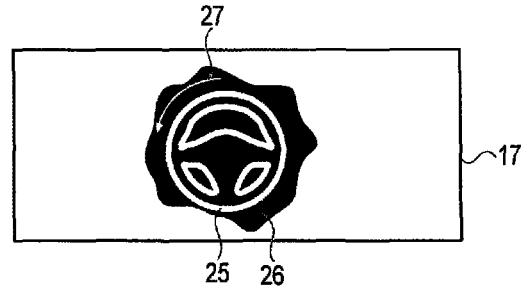

For example, when a transition is to be made from autonomous driving to manual driving, as shown in FIG. 11(a), a vehicle information presenting apparatus of the present invention may present, on the display 17, an image 25 shaped like a steering wheel and a background image 26 making an irregular motion behind the image 25. Thereby, the vehicle information presenting apparatus can call for attention from the driver, prompting the driver to take over and drive manually. By looking at the image 25, the driver can know at a single glance that he or she has to control the steering wheel now. The image 25 may be shaped like a pedal instead of a steering wheel. The color of the image 26 is not limited, and can be changed according to the degree of necessity to transition to manual driving. For example, the image 26 may be green when the degree of necessity to transition to manual driving is low, and may be red when the degree of necessity to transition to manual driving is high. In addition, as shown in FIG. 11(b), the vehicle information presenting apparatus may present, as an image 27, the direction in which the driver is to turn the steering wheel to transition to manual driving. This allows the driver to make a smooth transition to manual driving.

REFERENCE SIGNS LIST

9 system condition determiner
10 microphone (voice detector)
11 camera (image capturing unit)
12 heart rate measurement unit
13 conversation determination unit (occupant condition detector)
14 alertness level determiner (occupant condition detector)
15 driving attention level estimator
16 information presentation controller
23 pressure sensor (posture detector)
24 posture determiner (occupant condition detector)

The invention claimed is:

1. A vehicle information presenting apparatus for use in an autonomous vehicle that switches driving control between autonomous driving control, in which the autonomous vehicle is driven autonomously, and manual driving control, in which the autonomous vehicle is driven manually by a driver, the vehicle information presenting apparatus comprising:
   a driving attention level estimator configured to estimate a driving attention level of the driver; and
   an information presentation controller configured to switch image information to present to the driver according to the driving attention level of the driver estimated by the driving attention level estimator, wherein
   the information presentation controller switches between autonomous driving system condition information and driving assistance information for transitioning from autonomous driving to manual driving.

2. The vehicle information presenting apparatus according to claim 1, further comprising:

a system condition determiner configured to determine an autonomous driving system condition, wherein the information presentation controller presents the autonomous driving system condition to the driver when the driving attention level of the driver is equal to or lower than a first predetermined value.

3. The vehicle information presenting apparatus according to claim 2, wherein the system condition determiner calculates a system confidence level for the system condition, and when the system confidence level is equal to or lower than a second predetermined value, the information presentation controller presents, to the driver, information indicating that the system condition is unfavorable.

4. The vehicle information presenting apparatus according to claim 2, wherein the system condition determiner calculates a system confidence level for the autonomous driving system condition, and when the system confidence level is higher than a second predetermined value, the information presentation controller presents, to the driver, information indicating that the autonomous driving system condition is favorable.

5. The vehicle information presenting apparatus according to claim 1, further comprising an occupant condition detector configured to detect a condition of an occupant including the driver and thereby estimates the driving attention level of the driver.

6. The vehicle information presenting apparatus according to claim 5, wherein the occupant condition detector includes a voice detector configured to detect voice in a vehicle compartment, and the driving attention level estimator estimates the driving attention level of the driver based on the voice detected by the voice detector.

7. The vehicle information presenting apparatus according to claim 6, wherein the occupant condition detector detects voice of the driver and voice other than that of the driver from the voice in the vehicle compartment, and further detects at least one of a length of time from the voice of the occupant other than the driver to the voice of the driver, a speed of speech of the driver, and pitch fluctuation of the driver.

8. The vehicle information presenting apparatus according to claim 6, wherein the occupant condition detector further includes an image capturing unit configured to capture a facial image of the driver, and a heart rate measurement unit configured to measure a heart rate of the driver, and the driving attention level estimator estimates the driving attention level of the driver based on the facial image captured by the image capturing unit, the heart rate measured by the heart rate measurement unit, and the voice in the vehicle compartment.

9. The vehicle information presenting apparatus according to claim 8, wherein from the facial image, the occupant condition detector detects at least one of a pupil diameter, a yawning frequency, a blink length, and an eye-rubbing frequency.

10. The vehicle information presenting apparatus according to claim 5, wherein the occupant condition detector includes a posture detector configured to detect a posture of the occupant, and the driving attention level estimator estimates the driving attention level of the occupant based on the posture detected by the posture detector.

11. The vehicle information presenting apparatus according to claim 1, wherein the information presentation controller presents driving assistance information to the driver when the driving attention level of the driver is higher than a first predetermined value.

12. The vehicle information presenting apparatus according to claim 11, wherein the driving assistance information is information related to an operation to be performed by the driver when a transition is made from autonomous driving to manual driving.

13. The vehicle information presenting apparatus according to claim 2, wherein when the system condition determiner determines that the autonomous driving system condition is abnormal, the information presentation controller presents, to the driver, information indicating that the autonomous driving system condition is abnormal.

14. A vehicle information presenting apparatus for use in an autonomous vehicle that switches driving control between autonomous driving control, in which the autonomous vehicle is driven autonomously, and manual driving control, in which the autonomous vehicle is driven manually by a driver, the vehicle information presenting apparatus comprising:

a driving attention level estimator configured to estimate a driving attention level of the driver;

an information presentation controller configured to switch image information to present to the driver according to the driving attention level of the driver estimated by the driving attention level estimator; and a system condition determiner configured to determine an autonomous driving system condition, wherein the information presentation controller presents the autonomous driving system condition to the driver when the driving attention level of the driver is equal to or lower than a first predetermined value, the system condition determiner calculates a system confidence level for the system condition, and when the system confidence level is equal to or lower than a second predetermined value, the information presentation controller presents, to the driver, information indicating that the system condition is unfavorable.

15. A vehicle information presenting apparatus for use in an autonomous vehicle that switches driving control between autonomous driving control, in which the autonomous vehicle is driven autonomously, and manual driving control, in which the autonomous vehicle is driven manually by a driver, the vehicle information presenting apparatus comprising:

a driving attention level estimator configured to estimate a driving attention level of the driver;

an information presentation controller configured to switch image information to present to the driver according to the driving attention level of the driver estimated by the driving attention level estimator; and an occupant condition detector configured to detect a condition of an occupant including the driver and thereby estimates the driving attention level of the driver, wherein the occupant condition detector includes a voice detector configured to detect voice in a vehicle compartment, and the driving attention level estimator estimates the driving attention level of the driver based on the voice detected by the voice detector.

* * * * *